US006714805B2

(12) United States Patent
Jeon et al.

(10) Patent No.: US 6,714,805 B2
(45) Date of Patent: Mar. 30, 2004

(54) METHOD AND APPARATUS FOR NONINVASIVELY MONITORING HEMOGLOBIN CONCENTRATION AND OXYGEN SATURATION

(75) Inventors: Kye-jin Jeon, Suwon (KR); Gil-won Yoon, Seoul (KR)

(73) Assignee: Samsung Electronics Co., Ltd., Kyungki-do (KR)

( * ) Notice: Subject to any disclaimer, the term of this patent is extended or adjusted under 35 U.S.C. 154(b) by 0 days.

(21) Appl. No.: 10/125,740

(22) Filed: Apr. 19, 2002

(65) Prior Publication Data

US 2003/0009090 A1 Jan. 9, 2003

(30) Foreign Application Priority Data

Apr. 19, 2001 (KR) ........................................ 2001-21124

(51) Int. Cl.[7] .................................................. A61B 5/00
(52) U.S. Cl. ...................................... 600/323; 600/335
(58) Field of Search ................................ 600/309–310, 600/322–326, 335, 328

(56) References Cited

U.S. PATENT DOCUMENTS

| 5,277,181 | A | | 1/1994 | Mendelson et al. | |
|---|---|---|---|---|---|
| 5,348,003 | A | * | 9/1994 | Caro | 600/310 |
| 5,499,627 | A | | 3/1996 | Steuer et al. | |
| 5,720,284 | A | | 2/1998 | Aoyagi et al. | |
| 5,755,226 | A | | 5/1998 | Carim et al. | |
| 5,803,908 | A | * | 9/1998 | Steuer et al. | 600/314 |
| 5,823,951 | A | * | 10/1998 | Messerschmidt | 600/322 |
| 5,983,120 | A | * | 11/1999 | Groner et al. | 600/310 |
| 6,151,516 | A | * | 11/2000 | Kiani-Azarbayjany et al. | 600/322 |
| 6,181,958 | B1 | * | 1/2001 | Steuer et al. | 600/322 |
| 6,484,044 | B1 | * | 11/2002 | Lilienfeld-Toal | 600/316 |

FOREIGN PATENT DOCUMENTS

JP  4-40940  2/1992

OTHER PUBLICATIONS

US 5,292,788, 2/1995, Hudspeth (withdrawn)*
Optical Properties of Tissues with Strong (Multiple) Scattering pp. 3–11.
Design of Pulse Oximeters, pp. 46–51.
Steinke et al. IEEE Transactions on Biomedical Engineering, vol. BME–33, No. 3, Mar. 1986.
Twersky, Journal of the Optical Society of America, vol. 52, No. 2, Feb. 1962; pp. 145–171.
Chapter 9—Diffusion Approximation, pp. 175–190.

(List continued on next page.)

Primary Examiner—Max F. Hinderburg
Assistant Examiner—Matthew Kremer
(74) Attorney, Agent, or Firm—Lee & Sterba, P.C.

(57) ABSTRACT

A method and apparatus for noninvasively monitoring hemoglobin concentration and oxygen saturation, wherein the method includes selecting at least two wavelengths from a region of wavelengths in which an extinction coefficient for water is smaller that for hemoglobin, the at least two wavelengths including at least two isobestic wavelengths; sequentially radiating incident light beams having the selected wavelengths onto a predetermined site of a body which includes a blood vessel; receiving, at another site of the body, light beams sequentially transmitted through the predetermined site and converting the received light beams into electrical signals; calculating the light attenuation variation caused by pulses of blood for the respective wavelengths from the electrical signals; obtaining at least one ratio of the light attenuation variation between the selected wavelengths; and calculating the hemoglobin concentration $C_{Hb}$ in blood using the calculated at least one ratio of the light attenuation variation between the wavelengths.

27 Claims, 7 Drawing Sheets

OTHER PUBLICATIONS

Jeon et al.—Journal of Biomedical Optics 7(1), 45–50, Jan. 2002, pp. 45–50.

Tissue Optics, "Optical Properties of Tissues with Strong (Multiple) Scattering", Chapter 1, pp. 3–11, Valery Tuchin, (2000).

Webster, J.G., Design of Pulse Oximeters, (Chapter 4) Light Absorbance In Pulse Oximetry, pp. 46–51, Institute of Physics Publishing, (1997).

Steinke, John M., (and Shepherd, A.P.), "Role of Light Scattering in Whole Blood Oximetry", IEEE Transactions on Biomedical Engineering, vol. BME–33, No. 3, pp. 294–301, (Mar. 1986).

Twersky, Victor, "Multiple Scattering of Waves and Optical Phenomena", J. Optical Society of America, vol. 52, No. 2, pp. 145–171, (Feb. 1962).

Ishimaru, A, Wave Propagation and Scattering in Random Media, Chapter 9, "Diffusion Approximation", pp. 175–190, Adademic Press, (1978).

Jeon, Kye Jin, (and Kim, Su–Jin; Park, Kun Kook; Kim, Jong–Won; Yoon, Gilwon), "Noninvasive Total Hemoglobin Measurement", J. Biomedical Optics, vol. 7, No. 1, pp. 45–50, (Jan. 2002).

\* cited by examiner (a)          (b)

METHOD AND APPARATUS FOR NONINVASIVELY MONITORING HEMOGLOBIN CONCENTRATION AND OXYGEN SATURATION

BACKGROUND OF THE INVENTION

1. Field of the Invention

The present invention relates to monitoring a concentration of hemoglobin in a human body. More particularly, the present invention relates to a method and apparatus for noninvasively monitoring hemoglobin concentration and oxygen saturation in blood.

2. Description of the Related Art

Human blood consists of liquid plasma and three different corpuscles (i.e., red corpuscles, white corpuscles, and platelets). A primary function of the blood is to carry oxygen through the human body. Oxygen is essential to keep human body cells in a normal condition. If oxygen content is reduced, the metabolism of tissue cells is restricted. Furthermore, if oxygen is not supplied to the human body for a long time, body activity may stop. This critical oxygen supply function of the body relies essentially on the presence of hemoglobin in the red corpuscles. Accordingly, the total hemoglobin content in red corpuscles is considered to be a critical value in the clinical medicine field. Conventionally, the total hemoglobin content has been chemically analyzed by withdrawing blood from the human body. That is, hemoglobin concentration has been measured by a hemoglobin-cyanide method in clinical laboratories. However, a need exists for real-time monitoring of a patient's hemoglobin concentration in operating rooms or emergency rooms. In addition, females, pregnant females, growing children, and teenagers may require occasional measurements of their hemoglobin concentration values at home. Therefore, there is a need for measuring the hemoglobin concentration noninvasively without having to withdraw blood from the body.

Conventional methods of measuring hemoglobin concentration and oxygen saturation do not consider the scattering effects that occur because hemoglobin is present in red blood cells, which act to scatter incident light. Therefore, hemoglobin concentration and oxygen saturation cannot be measured accurately by conventional methods.

SUMMARY OF THE INVENTION

In an effort to solve the problems of conventional methods, it is a first feature of an embodiment of the present invention to provide a method for noninvasively accurately monitoring hemoglobin concentration and oxygen saturation by considering light scattering by red blood cells.

It is a second feature of an embodiment of the present invention to provide an apparatus for noninvasively accurately monitoring hemoglobin concentration and oxygen saturation by the above method.

The first feature of an embodiment of the present invention provides a method for noninvasively monitoring hemoglobin concentration and oxygen saturation including: (a) selecting at least two wavelengths from a region of wavelengths in which an extinction coefficient for water is smaller than an extinction coefficient for hemoglobin, the at least two wavelengths including at least two isobestic wavelengths; (b) sequentially radiating incident light beams having the selected wavelengths onto a predetermined site of a body that includes a blood vessel; (c) receiving, at another site of the body, light beams sequentially transmitted through the predetermined site and converting the received light beams into electrical signals; (d) calculating the light attenuation variation caused by pulses of blood for the respective wavelengths from the electrical signals; (e) obtaining at least one ratio of the light attenuation variation between the selected wavelengths; and (f) calculating the hemoglobin concentration $C_{Hb}$ in blood using the calculated at least one ratio of the light attenuation variation between the wavelengths.

The second feature of an embodiment of the present invention provides an apparatus for noninvasively monitoring hemoglobin concentration and oxygen saturation including: a light radiation unit for sequentially radiating incident light beams having at least two wavelengths selected from a region in which an extinction coefficient for water is smaller than an extinction coefficient for hemoglobin, onto a predetermined site of the body that includes a blood vessel; a photodetector unit for receiving, at another site of the body, light beams transmitted through the predetermined site, converting the received light beams into an electrical signal, and outputting the converted electrical signal; a variation calculation unit for calculating light attenuation variation for each of the selected at least two wavelengths from the electrical signal and outputting the calculated light attenuation variation; a ratio calculation unit for calculating at least one ratio among the light attenuation variations sequentially input from the variation calculation unit and outputting the calculated at least one ratio of the light attenuation variations; and a concentration calculation unit for calculating hemoglobin concentration in blood from the at least one ratio and outputting the calculated hemoglobin concentration, wherein the at least two wavelengths are externally selected to include at least two isobestic wavelengths.

BRIEF DESCRIPTION OF THE DRAWINGS

The above features and advantages of the present invention will become more apparent by describing in detail preferred embodiments thereof with reference to the attached drawings in which.

DETAILED DESCRIPTION OF THE INVENTION

Korean Patent Application No. 2001-21124, filed Apr. 19, 2001, and entitled: "Method and Apparatus for Noninvasively Monitoring Hemoglobin Concentration and Oxygen Saturation," is incorporated by reference herein in its entirety.

A method for noninvasively monitoring hemoglobin concentration and oxygen saturation, and the structure and operation of an apparatus for noninvasively monitoring hemoglobin concentration and oxygen saturation by the method according to the present invention will be described below with reference to the appended drawings.

Figure 1:
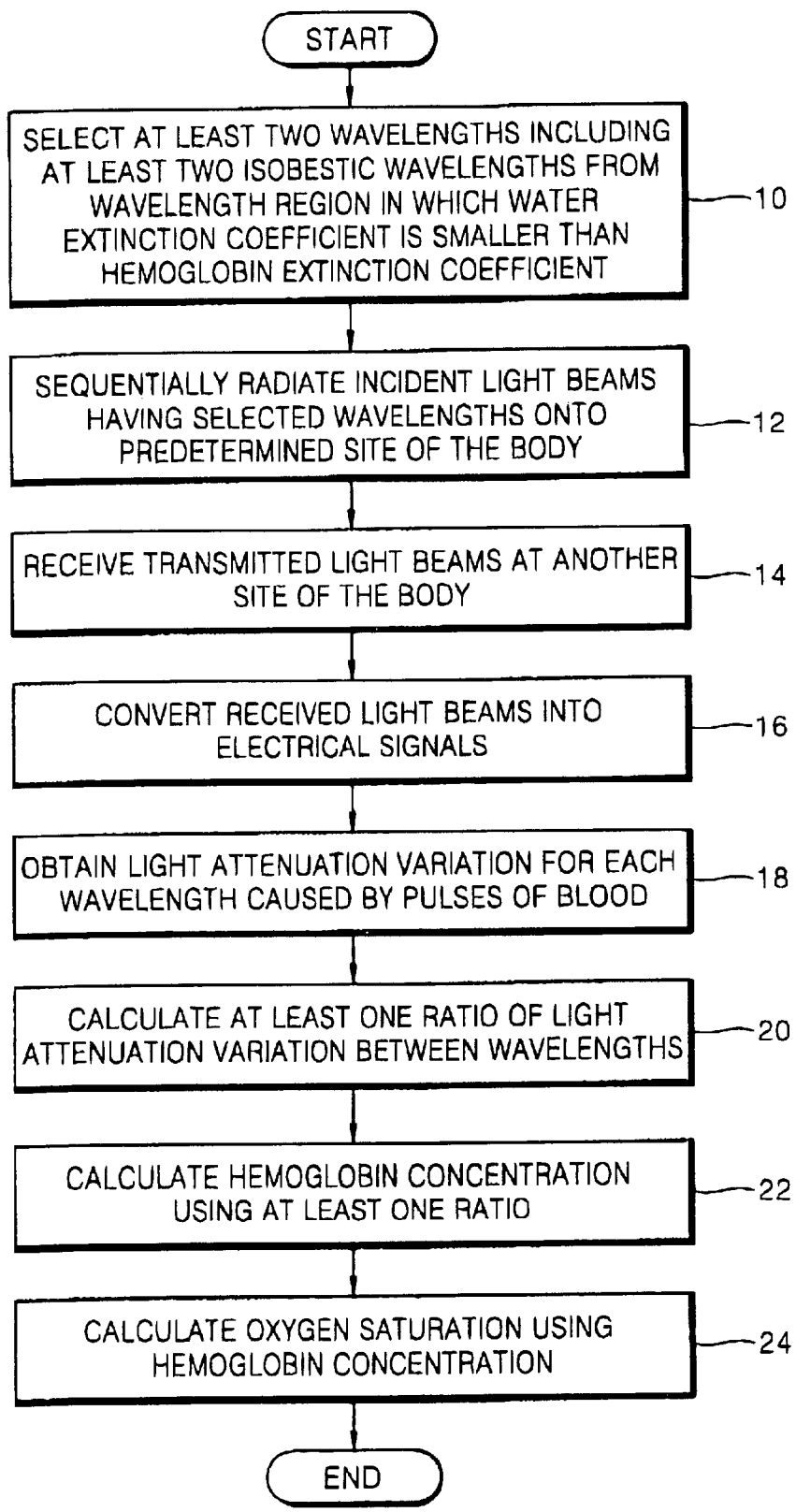
FIG. 1 is a flowchart illustrating a method for noninvasively measuring hemoglobin concentration and oxygen saturation according to an embodiment of the present invention.

FIG. 1 is a flowchart illustrating a method for noninvasively monitoring hemoglobin concentration and oxygen saturation according to an embodiment of the present invention. The method of FIG. 1 involves, in steps 10 and 12, sequentially radiating incident light beams having appropriately selected wavelengths onto a predetermined site of the body, in steps 14 through 18, calculating the light attenuation variation for each wavelength by receiving the incident light beams having passed sequentially through the predetermined site, and in steps 20 through 24, predicting hemoglobin concentration and oxygen saturation using the ratios of light attenuation variations for the wavelengths.

Figure 2:
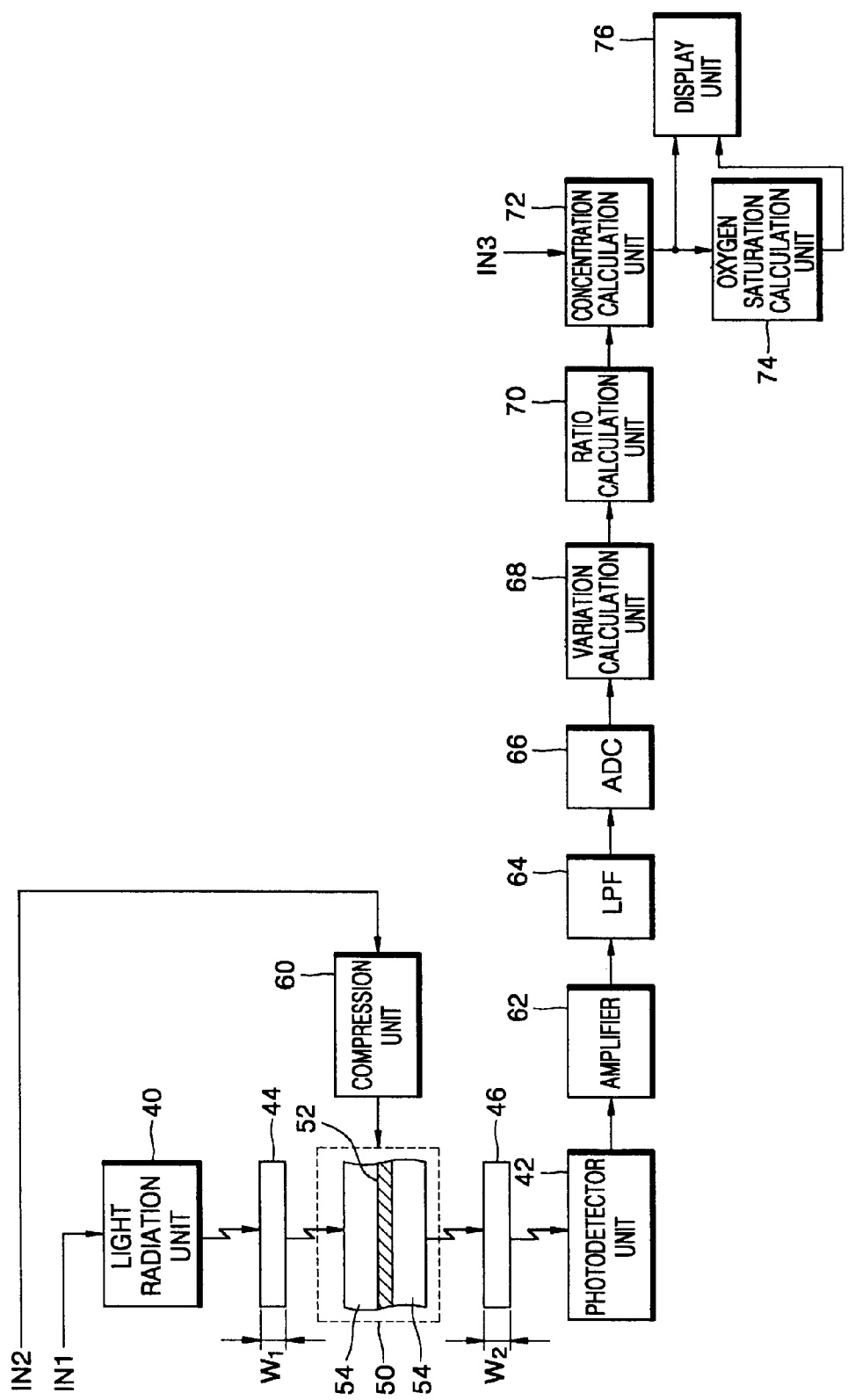
FIG. 2 is a block diagram of a preferred embodiment of an apparatus for noninvasively measuring hemoglobin concentration and oxygen saturation according to the present invention.

FIG. 2 is a block diagram of a preferred embodiment of an apparatus for noninvasively monitoring hemoglobin concentration and oxygen saturation for use in the method of FIG. 1. The apparatus of FIG. 2 includes a light radiation unit 40, a photodetector unit 42, a variation calculation unit 68, a ratio calculation unit 70, and a concentration calculation unit 72. The apparatus may further include correction members 44 and 46, a compression unit 60, an amplifier 62, a low-pass filter (LPF) 64, an analog-to-digital converter (ADC) 66, an oxygen saturation calculation unit 74, and a display unit 76.

The method for monitoring hemoglobin concentration according to an embodiment of the present invention is performed as follows.

In step 10, at least two wavelengths are selected from the wavelength region in which the extinction coefficient for water is smaller than the extinction coefficient for hemoglobin, i.e., from wavelengths no longer than 1300 nm.

Figure 3:
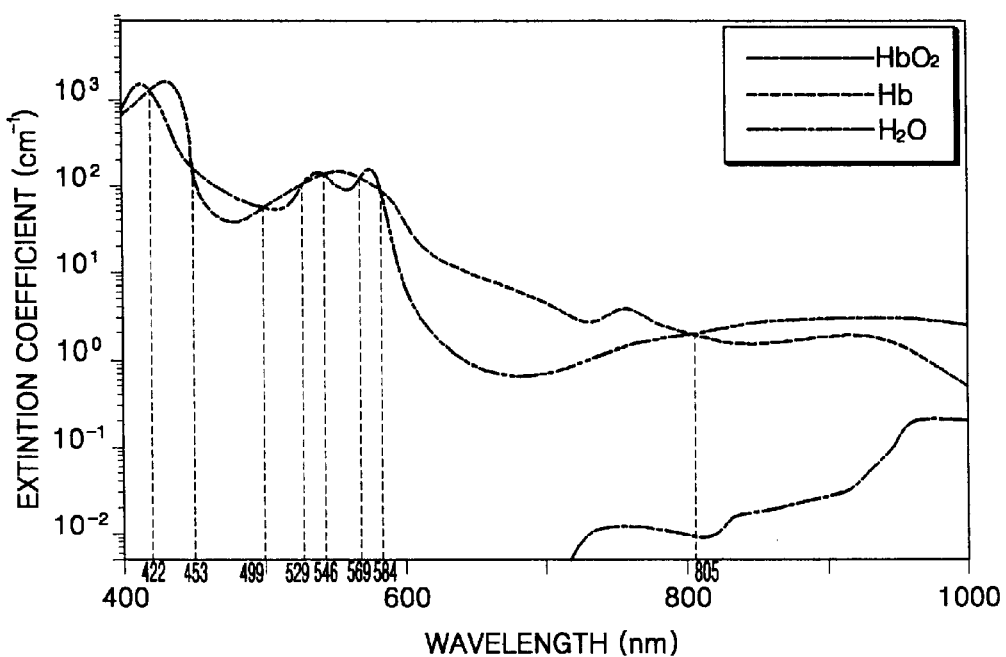
FIG. 3 is a graph showing the spectra of an extinction coefficient for oxyhemoglobin and deoxyhemoglobin.

FIG. 3 is a graph showing the spectra of extinction coefficient for oxyhemoglobin and deoxyhemoglobin, in which the vertical axis denotes extinction coefficients and the horizontal axis denotes wavelengths.

According to an embodiment of the present invention, the at least two wavelengths selected in step 10 include at least two isobestic wavelengths $\lambda_1$ and $\lambda_2$. Once two wavelengths are selected in step 10, both of the selected two wavelengths are considered to be isobestic. Here, "isobestic wavelength" indicates a wavelength having the same extinction coefficient irrespective of the form of hemoglobin as shown in FIG. 3, i.e., irrespective of whether hemoglobin is oxidized or reduced. As shown in FIG. 3, the isobestic wavelength may be 422 nm, 453 nm, 499 nm, 529 nm, 546 nm, 569 nm, 584 nm, 805 nm, or 1300 nm (not shown).

After step 10, in step 12, referring again to FIG. 2, the light radiation unit 40 sequentially radiates incident light beams having the selected wavelengths onto a predetermined site 50 of the body having a soft tissue 54 and a blood vessel 52. Here, the light radiation unit 40 receives information on the wavelengths selected in step 10 through an input port IN1, analyses the received information, and radiates incident light beams having corresponding wavelength(s) according to the result of the analysis onto the predetermined site 50. To this end, the light radiation unit 40 may be implemented by a light emitting diode (LED), a laser diode (Ld), or a lamp. Here, the predetermined site 50 may be any site of the body, for example, a finger or a toe.

After step 12, in step 14, the photodetector unit 42 receives the light beams having sequentially transmitted through the predetermined site 50 at a particular site of the body. After step 14, in step 16, the received light beams are converted into electrical signals. To perform steps 14 and 16, the photodetector unit 42 receives the light beams transmitted through the predetermined site 50 at the particular site of the body, converts the received light beams into electrical signals, and outputs the converted electrical signals. Here, according to an embodiment of the present invention, the light radiation unit 40 may be implemented by a photodiode that is formed of silicon (Si), germanium (Ge), or indium gallium arsenate (InGaAs) and sequentially radiates the incident light beams onto the predetermined site 50.

After step 16, in step 18, the variation calculation unit 68 calculates the light attenuation variation for each wavelength using the electrical signals input from the photodetector unit 42 and outputs the calculated light attenuation variation for each wavelength to the ratio calculation unit 70. Next, according to an embodiment of the present invention, the variation calculation unit 68 calculates the light attenuation variation for each wavelength as a ratio of the time variant component (AC) to the time invariant component (DC) of the electrical signal input from the photodetector unit 42.

The apparatus of FIG. 2 may further include the amplifier 62, the LPF 64, and the ADC 66 between the photodetector unit 42 and the variation calculation unit 68. The amplifier 62 amplifies the respective electrical signals output from the photodetector unit 42 and outputs the amplified electrical signals to the LPF 64. Then, the LPF 64 filters a low-frequency component of the respective electrical signals amplified by the amplifier 62 and outputs the filtered low-frequency component to the ADC 66. The ADC 66 converts the low-frequency component, which is in analog form, output from the LPF 64 into a digital form and outputs the converted digital low-frequency component to the variation calculation unit 68. Accordingly, the variation calculation unit 68 calculates the light attenuation variation for each wavelength from the digital low-frequency component input from the ADC 66.

After step 18, in step 20, the ratio calculation unit 70 calculates at least one ratio $R_{12}$, $R_{21}$, . . . between the light attenuation variations $R_1$, $R_2$, . . . for the wavelengths $\lambda_1$, $\lambda_2$, . . . , which are input sequentially from the variation calculation unit 68, and outputs the calculated at least one ratio to the concentration calculation unit 72.

To facilitate a description of steps 18 and 20, it is assumed that the two wavelengths $\lambda_1$ and $\lambda_2$ are selected in step 10, the predetermined site 50 of the body is a finger, and respective incident light beams radiated onto the finger are transmitted through the blood vessel 52 (path A) and do not pass the blood vessel 52 (path B). The light attenuation variation $R_1$ is calculated in the variation calculation unit 68 when the incident light beam having the wavelength $\lambda_1$ is radiated onto the predetermined site 50. The light attenuation variation $R_2$ is calculated in the variation calculation unit 68 when the incident light beam having the wavelength $\lambda_2$ is radiated onto the predetermined site 50. The ratio $R_{12}$ (=$R_1/R_2$) between the light attenuation variations is calculated in the ratio calculation unit 70. Calculation of $R_1$, $R_2$ and $R_{12}$ will be described in greater detail below with reference to appended drawings.

Figure 4:
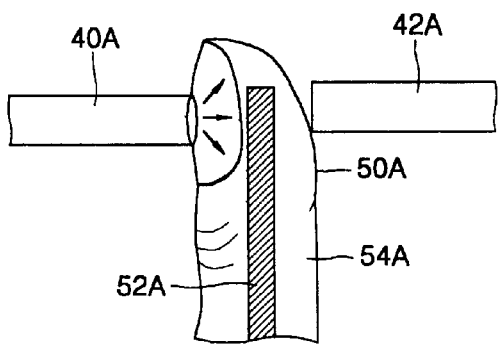
FIG. 4 illustrates a front view of a finger as a model for illustrating steps 18 and 20 of FIG. 1.

FIG. 4 is a front view of a finger 50A as a model for illustrating steps 18 and 20 of FIG. 1, in which a blood vessel 52A and a soft tissue 54A of the finger 50A, a light radiation unit 40A, and a photodetector unit 42A are shown.

Figure 5:
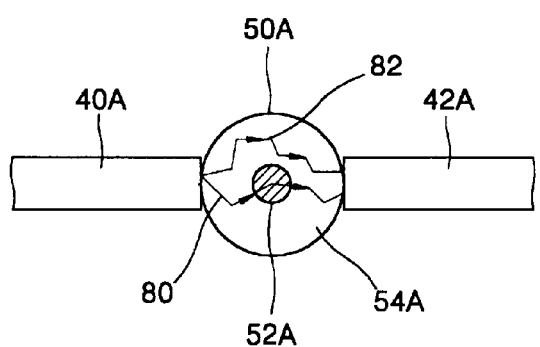
FIG. 5 illustrates a plan view of the finger shown in FIG. 4.

FIG. 5 is a plan view of the finger 50A shown in FIG. 4, in which the blood vessel 52A, the soft tissue 54A, the light radiation unit 40A, and the photodetector unit 42A are shown.

Referring to FIGS. 4 and 5, when the light radiation unit 40A radiates incoherent incident light beams onto the arteriole present at the end of the finger 50A, the incident light beams are substantially scattered while propagating through the soft tissue 54A and a bone area and become almost isotropically incident on the blood vessel 52A that is an arteriolar blood vessel. The intensities of the incident light beams are modulated while passing through the blood vessel 52A, whose thickness varies with pulses of blood pumped through the blood vessel 52A, and undergo multiple scattering while emerging from the soft tissue 54A due to the variation in the amount of blood according to the pulsation.

As described above, when the incident light beams radiated from the light radiation unit 40A onto the finger 50A travel along path A (corresponding to a path 80 of FIG. 5), the incident light beams reach the blood vessel 52A and experience modulation by pulsation. Meanwhile, when the incident light beams travel along path B (corresponding to a path 82 of FIG. 5), the incident light beams do not experience pulsation. Denoting the radius of the blood vessel 52A as $r_a$ and the radius of the finger 50A as $r_b$, the total time-invariant component DC of the transmitted light beams detected by the photodetector unit 42A consists of the time-invariant component $DC_a$ of the light beam transmitted through the path 80 and the time-invariant component $DC_b$ of the light beam transmitted through the path 82, as expressed by formula (1) below:

$$DC = DC_a + DC_b \quad (1)$$

where $DC_a$ is expressed by formula (2):

$$DC_a = f(r_a, r_b, \lambda) DC \quad (2)$$

where $f(r_a, r_b, \lambda)$ is a constant as a factor dependent upon the structure of the finger 50A including the blood vessel, and $\lambda$ is the wavelength of an incident light beam. Because the blood volume varies with pulsation of blood vessel 52A, the intensity of the light beam transmitted through the finger 50A is modulated by the light attenuation variation $\Delta OD_{tot}$. Here, the light attenuation variation $\Delta OD_{tot}$ is for the light beam passed through path 80 and is expressed by formula (3) below:

$$\Delta OD_{tot} = AC/DC_a = f^{-1}(r_a, r_b, \lambda) AC/DC \quad (3)$$

Here, it is difficult to accurately measure $f(r_a, r_b, \lambda)$. Therefore, the light attenuation variations $R_1$ and $R_2$ for two wavelengths $\lambda_1$ and $\lambda_2$ are measured, and the ratio $R_{12}$ (=$R_1/R_2$) of the variations $R_1$ and $R_2$ is calculated by formula (4) to eliminate the need for accurate measurement of $f(r_a, r_b, \lambda)$:

$$R_{12} = \frac{R_1}{R_2} = \frac{\Delta OD_{tot,\lambda 1}}{\Delta OD_{tot,\lambda 2}} = \frac{AC_{\lambda 1}/DC_{\lambda 1}}{AC_{\lambda 2}/DC_{\lambda 2}} \quad (4)$$

where $AC_{\lambda 1}$ and $AC_{\lambda 2}$ are the time-variant components of the wavelengths $\lambda_1$ and $\lambda_2$, respectively, and $DC_{\lambda 1}$ and $DC_{\lambda 2}$ are the time-invariant components of the wavelengths $\lambda_1$ and $\lambda_2$, respectively. Formula (4) above may be obtained, for example, through the method used in a pulse oximeter. The method used in pulse oximetry is disclosed in a book entitled "Design of Pulse Oximeter" (Chapter 4) by J. G. Webster, Institute of Physics Publishing, 1997.

As shown in formula (4) above, in step 18, the variation calculation unit 68 divides the time-variant components $AC_{\lambda 1}$ and $AC_{\lambda 2}$ of the electrical signals input from the photodetector unit 42 by the time-invariant components $DC_{\lambda 1}$ and $DC_{\lambda 2}$ of the wavelengths $\lambda_1$ and $\lambda_2$, respectively, to calculate the light attenuation variations $\Delta OD_{tot,\lambda 1}$ and $\Delta OD_{tot,\lambda 2}$ for the wavelengths $\lambda_1$ and $\lambda_2$. In step 20, the ratio $R_{12}$ calculation unit 70 divides the light attenuation variation $\Delta OD_{tot,\lambda 1}$ for the wavelength $\lambda_1$ by the light attenuation variation $\Delta OD_{tot,\lambda 2}$ for the wavelength $\lambda_2$ to calculate a ratio of light attenuation variation between the two wavelengths $\lambda_1$ and $\lambda_2$.

Hereinafter, an embodiment of step 10 of selecting at least two most appropriate wavelengths according to an embodiment of the present invention will be described below.

Figure 6:
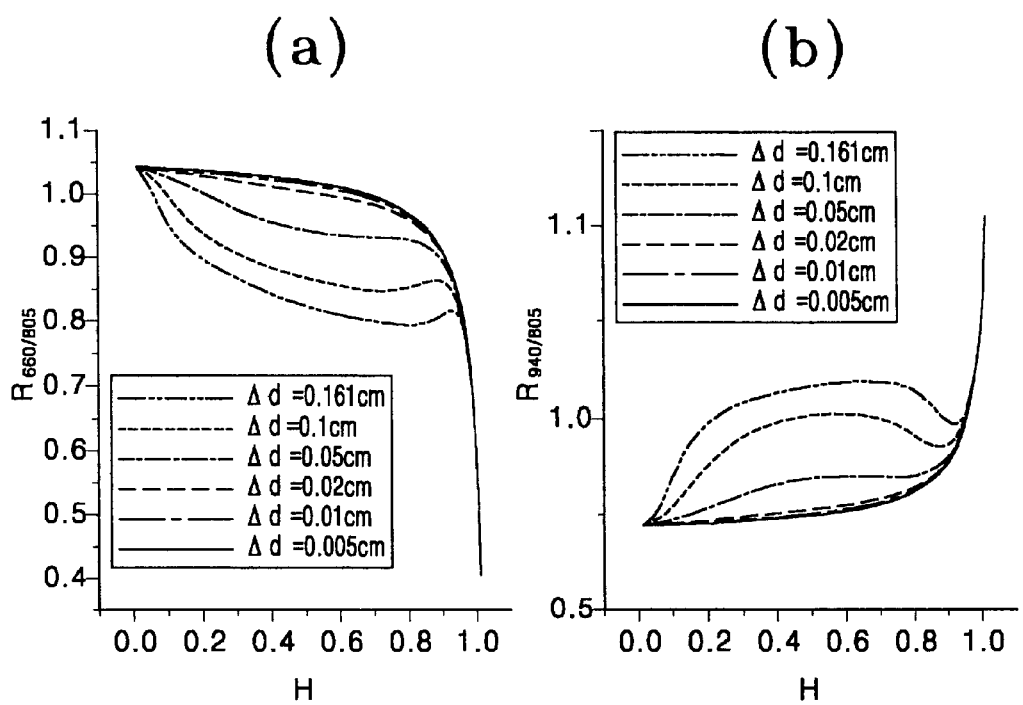
FIGS. 6a and 6b are graphs illustrating the results of simulation for the ratio of light attenuation variation for two sets of wavelengths with respect to a hematocrit value (H) and a thickness variation $\Delta d$ of a blood vessel.

FIGS. 6a and 6b are graphs illustrating the results of simulation for the ratio $R_{12}$ of light attenuation variation for two sets of wavelengths with respect to hematocrit value (H) and thickness variation $\Delta d$ of the blood vessel 52. In particular, FIG. 6a shows the ratio ($R_{660/805}$) of light attenuation variation for a set of wavelengths 660 nm and 805 nm, and FIG. 6b shows the ratio ($R_{940/805}$) for a set of wavelengths 940 nm and 805 nm.

The ratio $R_{12}$ of light attenuation variation for two sets of wavelengths, i.e., one set of wavelengths 940 nm and 805 nm and the other set of wavelengths 660 nm and 805 nm, is shown in FIGS. 6a and 6b, with respect to the variation in thickness $\Delta d$ of the blood vessel using parameters obtained from an experiment conducted by J. M. Steinke, et al. The experiment by J. M. Steinke, et al. is disclosed in an article entitled "Role of Light Scattering in Whole Blood Oximetry", IEEE Transactions on Biomedical Engineering Vol. BME-33, No. 3, March 1986, by John M. Steinke and A. P. Shepherd. As shown in FIGS. 6a and 6b, it is apparent that the ratio $R_{12}$ of light attenuation variation between two wavelengths is dependent upon the hematocrit value H and varies according to the thickness variation $\Delta d$ of the blood vessel. The value of $\Delta d$ and the $R_{12}$ dependency on the hematocrit H are different for different people.

After step 20, in step 22, the concentration calculation unit 72 calculates hemoglobin concentration ($C_{Hb}$) in blood using at least one ratio $R_{12}$ of light attenuation variation between two wavelengths input from the ratio calculation unit 70, and outputs the calculated hemoglobin concentration ($C_{Hb}$).

In an embodiment of step 22 according to an embodiment of the present invention, when two wavelengths $\lambda_1$ and $\lambda_2$ are selected in step 10, the hemoglobin concentration ($C_{Hb}$) is calculated by formula (5) below using the ratio $R_{12}$ of light attenuation variation calculated in step 20:

$$C_{Hb} = \frac{35^2(\varepsilon_1 - R_{12}\varepsilon_2)}{k_1 a_1 - k_a a_a R_{12}} + 35 \qquad (5)$$

where $\gamma_1$ and $\gamma_2$ denote the extinction coefficients for the wavelengths $\lambda_1$ and $\lambda_2$, respectively, $k_1$ and $k_a$ are constants dependent upon the characteristics of scattering and absorbing the incident light beams at the predetermined site 50 and the wavelengths $\lambda_1$ and $\lambda_2$, and $a_1$ and $a_a$ are constants dependent upon the size of scattering particles, the refractive indexes of hemoglobin and plasma, and the wavelengths $\lambda_1$ and $\lambda_2$.

Formula (5) used in the present invention is derived as follows.

First, if light scattering is not considered, the logarithm of the ratio of the light intensity $I_V$, modulated by pulsation of blood and detected by the photodetector unit 42, to the light intensity $I_P$, detected by the photodetector unit 42 without being modulated by pulsation of blood, corresponds to the light attenuation variation $\Delta OD_{abs}$ caused by the pulsation-induced thickness variation $\Delta d$ of the blood vessel. A difference in the degree of attenuation variations (or optical density) between whole blood and a hemoglobin solution having the same hemoglobin concentration is due to light scattering. Light scattering occurs at a contact surface between two media, i.e., plasma and red blood cells, due to a difference in a refractive index between the plasma and the red blood cells. Additionally, light that is scattered once will likely be scattered continuously by other adjacent red blood cells. Thus, the optical properties of whole blood are very complex and difficult to deal with as compared to the hemoglobin solution.

Conventionally, there are two approaches to explain the scattering effect of whole blood. The first approach, Twersky's theory, explains light scattering from large particles having a relatively low refractive index and high absorption in considering the wavelength of a radiated light beam. Twersky's theory is described in an article entitled "Multiple Scattering of Waves and Optical Phenomena" by Victor Twersky, Journal of the Optical Society of America, Vol. 52(2), February 1962. The second approach, the photon diffusion theory, explains the distribution of light intensity in media when the intensity of fully diffused optical flux varies due to absorption by and scattering from particles. The photon diffusion theory is described in a book entitled "Wave Propagation and Scattering in Random Media" by A. Ishimaru, Academic Press, Vol. 1, Chapter 9, Academic Press, 1978.

Because the variation of thickness d of the blood vessel 52 is small in considering the mean free path for scattering, the photon diffusion theory is not suitable for explaining the scattering effect of whole blood. Thus, when a scattered light beam is incident on the blood vessel 52, the total light attenuation $OD_{tot}$ in consideration of back scattering can be expressed as formula (6) below by the Twersky's equation:

$$OD_{tot} = \log\left(\frac{I_o}{I}\right) = \qquad (6)$$
$$\varepsilon CD - \log\left[(1-q)10^{-aDH(1-H)} + q10^{-2q'\varepsilon CDaDH(1-H)/(2\varepsilon CD+aDH(1-H))}\right]$$

where I and $I_O$ denote the intensities of transmitted and incident light beams, respectively, $\epsilon$ is the extinction coefficient, C denotes the concentration of light absorbing components in blood, and a is a constant dependent upon the size of scattering particles, the refractive indexes $n_{Hb}$ and $n_{plasma}$ of hemoglobin and plasma, and the wavelength of the incident light beam and is expressed by formula (7):

$$a = (4\pi^2 L/\lambda^2)(n'-1)^2 \qquad (7)$$

where L is the shape factor of red blood cells, and $n' = n_{Hb}/n_{plasma}$. In formula (6) above, D denotes the optical path length of the cuvetter, which is a kind of blood container; q is a constant dependent upon the size of scattering particles, the refractive indexes $n_{Hb}$ and $n_{plasma}$ of hemoglobin and plasma, the wavelength of the incident light beam, and the aperture angle of a photodiode with which the photodetection unit 42 is implemented; and q' is a constant dependent upon the structure of light radiating and detecting parts and light scattering and absorption by the red blood cells and plasma, and particularly upon the wavelength and the spectroscopic property of the incident light beam.

The first term on the right-hand side of formula (6) represents the amount of light absorption while passing through the optical path length D when no scattering occurs in the medium. The second term represents the amount of light absorption while passing through the optical path length D extended by light scattering. In particular, $10^{-aDH(1-H)}$ in the second term represents the degree of light attenuation by scattering from red blood cells and $q10^{-2q'\varepsilon CDaDH(1-H)/(2\varepsilon CD+aDH(1-H))}$ and $-q10^{-aDH(1-H)}$ represent the amount of scattered light received by the photodetector unit 42, which is dependent upon the geometrical structure of the photodetector unit 42.

When the optical path length D becomes smaller, e.g., approaches $\Delta d$, the effect of back scattering decreases, q' approaches zero. In this case, when the light beam transmitted through the blood vessel 52 becomes anisotropic while passing again through a scattering medium, i.e., the soft tissue 54, formula (6) above may be approximated by formula (8) below:

$$\Delta OD_{tot} = \epsilon C \Delta d + ka\Delta dH(1-H) = \Delta OD_{abs} + \Delta OD_{scat} \qquad (8)$$

where k is a constant dependent upon the optical structure of light radiating and receiving parts (corresponding to the elements denoted by reference numerals 40, 44, 46, and 42 in FIG. 2), the light scattering and absorption properties of the predetermined site 50 of the body, and the wavelength of the incident light beam. The term $\Delta OD_{abs}$ denotes the light attenuation variation caused by absorption and $\Delta OD_{scat}$ denotes the light attenuation variation caused by scattering. As the thickness d of the blood vessel decreases, formula (8) better approximates formula (6). The ratio $R_{12}$ of light attenuation variation between the two wavelengths $\lambda_1$ and $\lambda_2$ is expressed by formula (9) below:

$$R_{12} = \frac{\varepsilon_1 C \Delta d + k_1 a_1 H(1-H)}{\varepsilon_2 C \Delta d + k_2 a_2 H(1-H)} = \frac{\Delta OD_{tot,\lambda 1}}{\Delta OD_{tot,\lambda 2}} = \frac{R_1}{R_2} \qquad (9)$$

If light absorption by hemoglobin is predominant while the incident light beams pass through the blood vessel 52, formula (10) below is generally satisfied:

$$\epsilon_1 C = \epsilon_{1,Hb} C_{Hb} \qquad (10)$$

where the hemoglobin concentration ($C_{Hb}$) is expressed in unit of grams/deciliter.

Here, the hemoglobin concentration ($C_{Hb}$) and the hematocrit value (H) have the relation of formula (11) below:

$$C_{Hb} \approx 35 \times H \qquad (11)$$

Substituting formulae (10) and (11) into formula (9) gives formula (12) below:

$$R_{12} = \frac{35\varepsilon_1 + k_1 a_1(1-H)}{35\varepsilon_2 + k_2 a_2(1-H)} = \frac{35\varepsilon_1 + k_1 a_1\left(1 - \frac{C_{Hb}}{35}\right)}{35\varepsilon_2 + k_2 a_2\left(1 - \frac{C_{Hb}}{35}\right)} \quad (12)$$

Formula (5) above may be derived by rearranging formula (12) to isolate the hemoglobin concentration ($C_{Hb}$).

Another preferred embodiment of step 22 according to an embodiment of the present invention will be described below.

Figure 7:
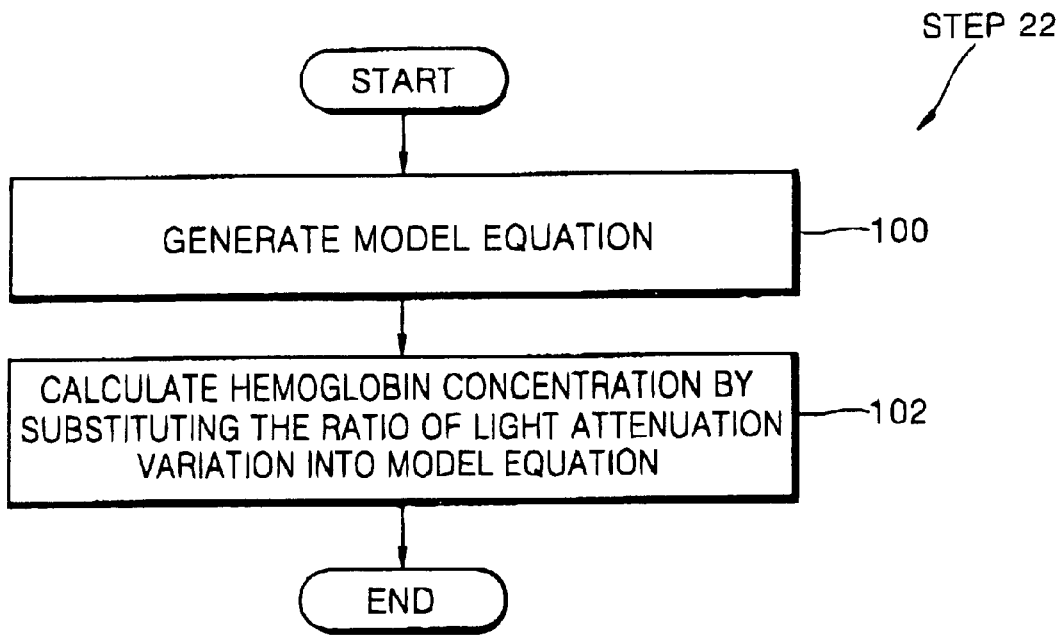
FIG. 7 is a flowchart illustrating a preferred embodiment of step 22 of the method of an embodiment of the present invention shown in FIG. 1.

FIG. 7 is a flowchart illustrating a preferred embodiment of step 22 of FIG. 1 according to an embodiment of the present invention, which includes steps 100 and 102 of calculating the hemoglobin concentration from at least one ratio of light attenuation variation between two wavelengths using a previously generated model equation.

Referring to FIG. 7, in step 100, the concentration calculation unit 72 derives the model equation expressed by formula (13) below based upon the relation between a hemoglobin concentration ($C_{Hb}$) invasively measured previously and then input through an input port IN3 (see FIG. 2) and the ratios of light attenuation variation previously calculated in step 20:

$$C_{Hb} = \sum_{i}^{p}\sum_{j}^{p} A_{ij} R_{ij}, \text{ where } R_{ij} = 1 \text{ if } i = j \quad (13)$$

where $A_{ij}$ is a coefficient for ratio $R_{ij}$; $R_{ij}$ is the ratio of light attenuation variation between wavelengths previously calculated in step 20; and p is an integer greater than or equal to 2. Here, according to an embodiment of the present invention, the coefficient $A_{ij}$ may be statistically obtained, for example, by a principle component regression (PCR) method or partial least squares regression (PLSR) method.

For example, when the ratio $R_{12}$ of light attenuation variation between wavelengths, which was noninvasively calculated previously, and the hemoglobin concentration ($C_{Hb}$) measured previously by invasively withdrawing blood samples are the same as in Table 1, the model equation of formula (13) is derived based upon the relation between the ratios $R_{12}$ and the hemoglobin concentration ($C_{Hb}$) shown in Table 1.

TABLE 1

| $R_{12}$ | $C_{Hb}$ |
|---|---|
| 0.80 | 24.50 |
| 0.85 | 10.50 |
| 0.90 | 5.25 |
| 0.95 | 3.50 |

In this case, if p=2, the model equation of formula (13) for the hemoglobin concentration ($C_{Hb}$) can be expressed as formula (14) below:

$$C_{Hb} = (R_1, R_2)\begin{pmatrix} A_{11} & A_{12} \\ A_{21} & A_{22} \end{pmatrix}\begin{pmatrix} \frac{1}{R_1} \\ \frac{1}{R_2} \end{pmatrix} = A_{11} + A_{22} + A_{21}R_1 + A_{12}R_{12} \quad (14)$$

After step 100, in step 102, the concentration calculation unit 72 calculates the hemoglobin concentration ($C_{Hb}$) by substituting the ratios $R_{12}, R_{21}, \ldots$ calculated in step 20 into the model equation of formula (13) and outputs the calculated hemoglobin concentration ($C_{Hb}$) to the oxygen saturation calculation unit 74 and the display unit 76.

In conclusion, the method and apparatus for noninvasively monitoring hemoglobin concentration according to an embodiment of the present invention considers several ratios $R_{ij}$ of light attenuation variation between wavelengths, which are expressed by formula (13) above, so that the hemoglobin concentration $C_{Hb}$ may be measured accurately by compensating for errors of the concentration.

The structure and operation of a preferred embodiment 72A of the concentration calculation unit 72 according to an embodiment of the present invention, which performs the embodiment of step 22 illustrated in FIG. 7, will now be described below.

Figure 8:
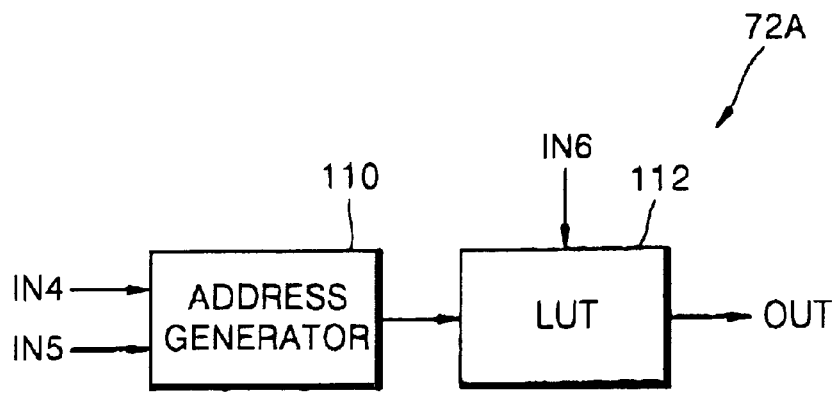
FIG. 8 is a block diagram of a preferred embodiment of the concentration calculation unit shown in FIG. 2 according to an embodiment of the present invention.

FIG. 8 is a block diagram of the preferred embodiment 72A of the concentration calculation unit 72 shown in FIG. 2 and includes an address generator 110 and a look-up table (LUT) 112.

The address generator 110 of FIG. 8 generates addresses based upon the relation between the real hemoglobin concentrations ($C_{Hb}$), which are invasively measured and externally input through an input port IN4, and the ratio ($R_{ij}$) of light attenuation variation between wavelengths, which are input through an input port IN5 from the ratio calculation unit 70, and outputs the generated addresses to the LUT 112.

Here, the LUT 112 outputs one of the real hemoglobin concentrations ($C_{Hb}$) externally input through an input port IN6 previously and stored therein through an output port OUT as a predicted hemoglobin concentration in response to an address input from the address generator 110.

Preferred embodiments of the present invention for very accurately measuring hemoglobin concentration will now be described below.

In a first embodiment, incident light beams may be sequentially radiated onto the predetermined site 50 with the application of pressure. Here, the pressure applied to the predetermined site 50 may be varied. To this end, the light radiation unit 40 having a predetermined weight may sequentially radiate incident light beams while contacting and compressing the predetermined site 50 by the weight of the light radiation unit 40.

In a second embodiment, the apparatus according to an embodiment of the present invention shown in FIG. 2 may further include a compression unit 60 for compressing the predetermined site 50. Here, the compression unit 60 externally receives, through an input port IN2, information on a variable pressure to be applied to the predetermined site 50, analyses the received information, and compresses the predetermined site 50 by the pressure determined according to the result of information analysis. As pressure from the compression unit 60 is applied to the predetermined site 50, the light radiation unit 40 sequentially radiates incident light beams onto the predetermined site 50.

In a third embodiment, a site of the body having a blood vessel whose thickness variation is not greater than a predetermined value, e.g., 500 μm, is selected as the predetermined site 50.

Figure 9:
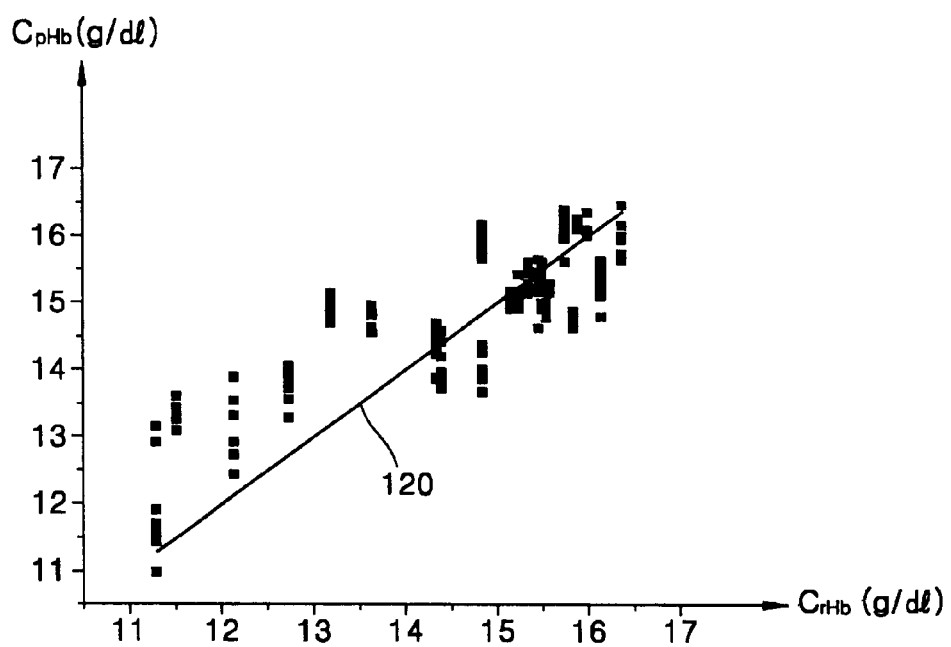
FIG. 9 is a graph illustrating the relation between a reference hemoglobin concentration ($C_{rHb}$) invasively measured in vivo and a hemoglobin concentration ($C_{pHb}$) noninvasively predicted in vivo with two wavelengths 569 nm and 805 nm selected in step 10 of FIG. 1.

FIG. 9 is a graph illustrating the relation between a reference hemoglobin concentration ($C_{rHb}$) invasively measured in vivo and a hemoglobin concentration ($C_{pHb}$) noninvasively predicted in vivo when two wavelengths 569 nm and 805 nm are selected in step 10.

As is apparent in FIG. 9, the hemoglobin concentration ($C_{pHb}$) (■) measured by the apparatus and method according to an embodiment of the present invention nearly approximates the reference value 120.

Additionally, the dynamic range of the ratio $R_{12}$ of light attenuation variation with respect to the variation of hematocrit (H) is very wide when the two wavelengths 569 nm and 805 nm are selected, so that the hematocrit (H) may be predicted accurately using the ratio $R_{12}$ of light attenuation variation between the two wavelengths. For example, conventional hemoglobin measuring methods determined the hematocrit (H) using wavelengths in the wavelength region in which water absorbance is even greater than hemoglobin absorbance. For this reason, two photodiodes respectively formed of Si and Ge (or InGaAs) were needed to implement a conventional hemoglobin concentration measuring apparatus. In this case, two wavelengths emitted from the two photodiodes have different optical paths. Nevertheless, the conventional hemoglobin concentration measuring methods determined hematocrit with the assumption that the two wavelengths used have the same optical path. Accordingly, accurate determination of hematocrit could not be achieved with the conventional methods. In contrast, because the method for monitoring hemoglobin concentration according to the present invention sequentially radiates incident light beams through the blood vessel 52 one by one, only one photodetector unit 42 implemented by Si, Ge, or InGaAs is used. As that method satisfies the assumption that two wavelengths used have the same optical path, hematocrit is accurately determined.

Next, in step 24, a method for monitoring oxygen saturation according to an embodiment of the present invention may calculate oxygen saturation S using the determined hemoglobin concentration $C_{Hb}$ after step 22. The oxygen saturation calculation unit 74 provided to calculate S calculates oxygen saturation S using the hemoglobin concentration $C_{Hb}$ input from the concentration calculation unit 72 and outputs the calculated oxygen saturation S to the display unit 76.

A preferred embodiment of step 24 of FIG. 1 performed in the oxygen saturation calculation unit 74 will be described below with reference to FIG. 10.

Figure 10:
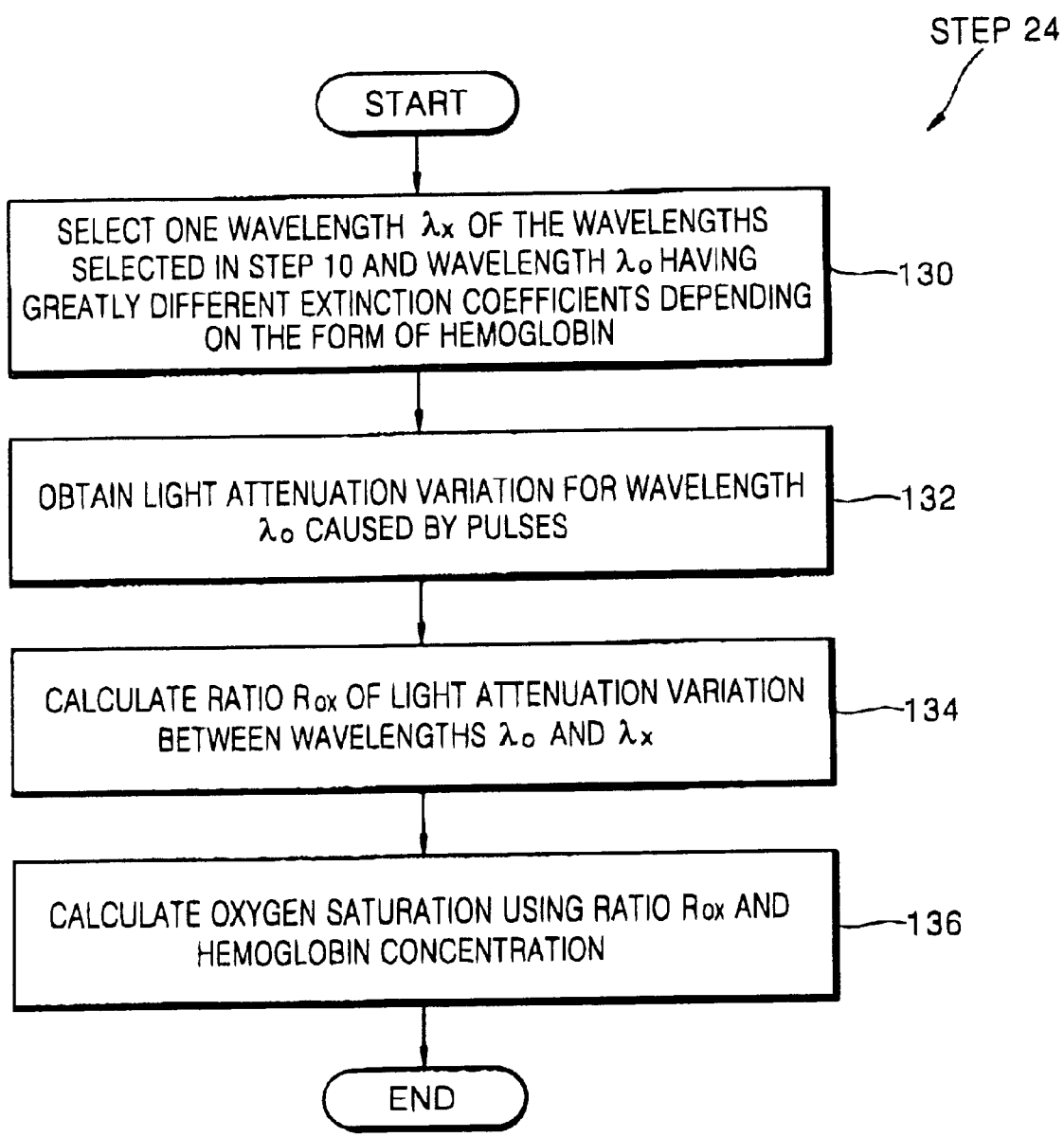
FIG. 10 is a flowchart illustrating a preferred embodiment of step 24 of the method according to the present invention shown in FIG. 1.

FIG. 10 is a flowchart illustrating a preferred embodiment of step 24 of FIG. 1 including steps 130, 132, 134 and 136 of calculating oxygen saturation S using the ratio of light attenuation variation between two appropriately selected wavelengths and the hemoglobin concentration.

Referring to FIG. 10, in step 130, in an embodiment for performing step 24, one wavelength $\lambda_X$ of the at least two wavelengths selected in step 10 and a wavelength $\lambda_O$ having greatly different extinction coefficients depending on the form of hemoglobin are selected. For example, the wavelength $\lambda_O$ may be 660 nm at which the difference between extinction coefficients for hemoglobin (Hb) and oxyhemoglobin (HbO$_2$) is greatest in FIG. 3, and the wavelength $\lambda_X$ may be 805 nm selected from the near infrared region of 800–950 nm.

After step 130, in step 132, the light attenuation variation $\Delta OD_{tot, \, go}$ for the selected wavelength $\lambda_O$ is obtained by performing steps 12 through 18 of FIG. 1. After step 132, in step 134, a ratio $R_{OX}$ of light attenuation variation between the wavelengths $\lambda_O$ and $\lambda_X$, i.e., $\Delta OD_{tot, \, \lambda_O}/\Delta OD_{tot, \, \lambda_X}$, is calculated.

After step 134, in step 136, oxygen saturation S in blood is calculated using the ratio $R_{OX}$ and the hemoglobin concentration $C_{Hb}$ calculated in step 22.

According to the present invention, the oxygen saturation S may be calculated by formula (15) below:

$$R_{OX} = \frac{[\varepsilon_{HbO_2,O}S + \varepsilon_{Hb,O}(1-S)]C_{Hb} + k_O a_O H(1-H)}{\varepsilon_{Hb,X}C_{Hb} + k_X a_X H(1-H)} \quad (15)$$

where $\varepsilon_{HbO_2,O}$ indicates the extinction coefficient for oxyhemoglobin (HbO$_2$) at the wavelength $\lambda_O$, $\varepsilon_{Hb,O}$ indicates the extinction coefficient for hemoglobin (Hb) at the wavelength $\lambda_O$; $\varepsilon_{Hb,X}$ indicates the extinction coefficient for hemoglobin (Hb) at the wavelength $\lambda_X$; $k_X$ and $k_O$ are constants dependent upon the characteristics of scattering and absorbing incident light beams at the predetermined site 50 and the wavelengths $\lambda_O$ and $\lambda_X$; and $a_X$ and $a_O$ are constants dependent upon the size of scattering particles, the refractive indexes $n_{Hb}$ and $n_{plasma}$ of hemoglobin and plasma, respectively, and the wavelengths $\lambda_O$ and $\lambda_X$.

Unlike a conventional method and apparatus, the method and apparatus for measuring oxygen saturation according to an embodiment of the present invention predicts oxygen saturation in consideration of the accurately measured hemoglobin concentration so that a measuring error for oxygen saturation S may be compensated for.

In addition, the apparatus for noninvasively monitoring hemoglobin concentration and oxygen saturation according to an embodiment of the present invention shown in FIG. 2 may further include the display unit 76. In this case, the display unit 76 displays the hemoglobin concentration $C_{Hb}$ input from the concentration calculation unit 72 and the oxygen saturation S input from the oxygen saturation calculation unit 74 to enable users to visually monitor the hemoglobin concentration and the oxygen saturation in the body.

The apparatus for noninvasively monitoring hemoglobin concentration and oxygen saturation according to an embodiment of the present invention shown in FIG. 2 may further include at least one of the correction members 44 and 46. In this case, the correction members 44 or 46 have light transmitting and scattering properties similar to the soft tissue 54 of the body and are disposed on the optical paths of the light beams incident on and transmitted through the predetermined site 50 and on the outside of the predetermined site 50. The thickness $W_1$ or $W_2$ of the correction member 44 or 46, respectively, on the external optical path may be varied. According to an embodiment of the present invention, correction member 44 or 46 may be implemented in the form of liquid implemented in the form of gel, with polystyrene beads, an intra-lipid, or a milk solution having similar scattering characteristics as in the body for the visible and near infrared rays. Preferably, the correction member 44 or 46 having the form of liquid may be implemented in the form of gel.

By using at least one of the correction members 44 and 46, the apparatus for monitoring hemoglobin concentration and oxygen saturation according to an embodiment of the present invention is able to physically compensate for errors in the measurement of hemoglobin concentration that could not be compensated for by varying the wavelengths used.

The method and apparatus for noninvasively monitoring hemoglobin concentration and oxygen saturation according to an embodiment of the present invention may measure not only the hemoglobin concentration in arteriolar blood using pulses in a noninvasive manner but also oxygen saturation through correction based on the accurate hemoglobin concentration.

As described above, the method and apparatus for noninvasively monitoring hemoglobin concentration and oxygen saturation according to an embodiment of the present invention is able to measure both the hemoglobin concentration and oxygen saturation in a noninvasive manner, without having to withdraw blood samples and without temporal and spatial limitations and also monitor the hemoglobin concentration and oxygen saturation in real time. Accordingly, the method and apparatus of the embodiments of the present invention have useful applications in operating rooms or emergency rooms. Unlike in conventional methods, water absorbance is not considered in the measurement of the hemoglobin concentration and oxygen saturation according to the present invention so that the hemoglobin concentration and oxygen saturation may be accurately measured without being influenced by variation in body liquid volume. In addition, the oxygen saturation may be more accurately determined by correcting the oxygen saturation using the accurately measured hemoglobin concentration. According to an embodiment of the present invention, only one photodetector unit 42, which may be implemented with a photodiode, is enough for the measurement in the present invention so that the cost may be reduced as compared to conventional methods that require two photodiodes. Both the wavelengths used in the present invention belong to the wavelength region that may be detected by a low-cost photodiode made of Si so that the cost may be further reduced. The use of only one photodetector unit 42 further increases accuracy in the measurement of hemoglobin concentration and oxygen saturation. In addition, there is no need to measure $f(r_a, r_b, \lambda)$ so that the hemoglobin concentration and oxygen saturation may be measured accurately and the measurement is less affected by body tissues other than the blood vessel 52.

While the present invention has been particularly shown and described with reference to preferred embodiments thereof, it will be understood by those of ordinary skill in the art that various changes in form and details may be made herein without departing from the spirit and scope of the present invention as defined by the appended claims.

What is claimed is:

1. A method for noninvasively monitoring hemoglobin concentration and oxygen saturation comprising:
   (a) selecting at least two wavelengths from a region of wavelengths in which an extinction coefficient for water is smaller than an extinction coefficient for hemoglobin, the at least two wavelengths including at least two isobestic wavelengths;
   (b) sequentially radiating incident light beams having the selected wavelengths onto a predetermined site of a body that includes a blood vessel, wherein the predetermined site includes the blood vessel whose thickness varies with pulses no greater than a predetermined value;
   (c) receiving, at another site of the body, light beams sequentially transmitted through the predetermined site and converting the received light beams into electrical signals;
   (d) calculating the light attenuation variation caused by pulses of blood for the respective wavelengths from the electrical signals;
   (e) obtaining at least one ratio of the light attenuation variation between the selected wavelengths; and
   (f) calculating the hemoglobin concentration $C_{Hb}$ in blood using the calculated at least one ratio of the light attenuation variation between the wavelengths.

2. The method as claimed in claim 1, wherein the at least two wavelengths selected in (a) comprise two wavelengths between which the difference in the light attenuation variation with respect to hematocrit H is greatest.

3. The method as claimed in claim 2, wherein the at least two wavelengths selected in (a) are 569 nm and 805 nm.

4. The method as claimed in claim 2, wherein the at least two wavelengths selected in (a) are 546 nm and 805 nm.

5. The method as claimed in claim 1, wherein the isobestic wavelengths are selected from the group consisting of 422 nm, 453 nm, 499 nm, 529 nm, 546 nm, 569 nm, 584 nm, 805 nm, and 1300 nm.

6. The method as claimed in claim 1, wherein the predetermined value is 500 µm.

7. The method as claimed in claim 1, wherein, in (b), the incident light beams are sequentially radiated while applying a variable pressure to the predetermined site.

8. The method as claimed in claim 1, wherein, in (d), the light attenuation variation for each wavelength caused by pulses of blood is obtained as a ratio between a time variant component and a time invariant component of the electrical signals.

9. The method as claimed in claim 1, wherein (f) comprises:
   (f1) generating the model equation below based upon the relation between hemoglobin concentrations measured invasively and the at least one ratio obtained in (e):

$$C_{Hb} = \sum_{i}^{p} \sum_{j}^{p} A_{ij} R_{ij}, \text{ where } R_{ij} = 1 \text{ if } i = j$$

where $A_{ij}$ is a coefficient for ratio $R_{ij}$; $R_{ij}$ is the ratio of the light attenuation variation between the wavelengths obtained in (e); and p is an integer greater than or equal to 2; and
   (f2) calculating the hemoglobin concentration $C_{Hb}$ by substituting the at least one ratio obtained in (e) into the model equation generated in (f1).

10. The method as claimed in claim 9, wherein, in (f), the coefficient $A_{ij}$ is statistically obtained by a principle component regression (PCR) method.

11. The method as claimed in claim 9, wherein, in (f), the coefficient $A_{ij}$ is statistically obtained by a partial least squares regression (PLSR) method.

12. A method for noninvasively monitoring hemoglobin concentration and oxygen saturation comprising:
   (a) selecting at least two wavelengths from a region of wavelengths in which an extinction coefficient for water is smaller than an extinction coefficient for hemoglobin, the at least two wavelengths including at least two isobestic wavelengths;
   (b) sequentially radiating incident light beams having the selected wavelengths onto a predetermined site of a body that includes a blood vessel;
   (c) receiving, at another site of the body, light beams sequentially transmitted through the predetermined site and converting the received light beams into electrical signals;
   (d) calculating the light attenuation variation caused by pulses of blood for the respective wavelengths from the electrical signals;
   (e) obtaining at least one ratio of the light attenuation variation between the selected wavelengths: and
   (f) calculating the hemoglobin concentration $C_{Hb}$ in blood using the calculated at least one ratio of the light attenuation variation between the wavelengths,
   wherein, when the at least two wavelengths selected in (a) are $\lambda_1$ and $\lambda_2$, the hemoglobin concentration $C_{Hb}$ is calculated in (f) by the formula below using a ratio $R_{12}$ of light attenuation variation between the two wavelengths $\lambda_1$ and $\lambda_2$ obtained in (e):

$$C_{Hb} = \frac{35^2(\varepsilon_1 - R_{12}\varepsilon_2)}{k_1 a_1 - k_a a_a R_{12}} + 35$$

where $\varepsilon_1$ and $\varepsilon_2$ denote the extinction coefficients for the wavelengths $\lambda_1$ and $\lambda_2$, respectively, $k_1$ and $k_a$ are constants dependant upon the characteristics of scattering and absorbing the incident light beams at the predetermined site and the wavelengths $\lambda_1$ and $\lambda_2$, and $a_1$ and $a_a$ are constants dependent upon the size of scattering particles, the refractive indexes of hemoglobin and plasma, and the wavelengths $\lambda_1$ and $\lambda_2$.

13. A method for noninvasively monitoring hemoglobin concentration and oxygen saturation comprising:
   (a) selecting at least two wavelengths from a region of wavelengths in which an extinction coefficient for water is smaller than an extinction coefficient for hemoglobin, the at least two wavelengths including at least two isobestic wavelengths;
   (b) sequentially radiating incident light beams having the selected wavelengths onto a predetermined site of a body that includes a blood vessel;
   (c) receiving, at another site of the body, light beams sequentially transmitted through the predetermined site and converting the received light beams into electrical signals;
   (d) calculating the light attenuation variation caused by pulses of blood for the respective wavelengths from the electrical signals;
   (e) obtaining at least one ratio of the light attenuation variation between the selected wavelengths;
   (f) calculating the hemoglobin concentration $C_{Hb}$ in blood using the calculated at least one ratio of the light attenuation variation between the wavelengths; and
   (g) calculating oxygen saturation S using the hemoglobin concentration $C_{Hb}$ calculated in (f), wherein (g) includes:
   (g1) selecting one wavelength $\lambda_X$ of the at least two wavelengths selected in (a) and a wavelength $\lambda_O$ having greatly different extinction coefficients depending upon the form of hemoglobin;
   (g2) obtaining the light attenuation variation for the wavelength $\lambda_O$ selected in (g1) by performing (b) through (d);
   (g3) obtaining a ratio $R_{OX}$ between the light attenuation variation for the wavelength $\lambda_O$, obtained in (g2) and the light attenuation variation for the wavelength $\lambda_X$ obtained in (d); and (g4) calculating the oxygen saturation S in blood using the ratio obtained in (g3) and the hemoglobin concentration $C_{Hb}$ calculated in (f),
wherein, in (g4), the oxygen saturation S is calculated by the formula below:

$$R_{OX} = \frac{[\varepsilon_{HbO_2,O}S + \varepsilon_{Hb,O}(1-S)]C_{Hb} + k_O a_O H(1-H)}{\varepsilon_{Hb,X} C_{Hb} + k_X a_X H(1-H)}$$

where $\varepsilon_{HbO_2,O}$ indicates an extinction coefficient for oxyhemoglobin at the wavelength $\lambda_O$; $\varepsilon_{Hb,O}$ indicates the extinction coefficient for hemoglobin at the wavelength $\lambda_O$; $\varepsilon_{Hb,X}$ indicates the extinction coefficient for hemoglobin at the wavelength $\lambda_X$; $k_X$ and $k_O$, are constants dependent upon the characteristics of scattering and absorbing the incident light beams at the predetermined site and the wavelengths $\lambda_O$, and $\lambda_X$, $a_X$ and $a_O$ are constants dependent upon the size of scattering particles, the refractive indexes of hemoglobin and plasma, and the wavelengths $\lambda_O$ and $\lambda_X$, and H denotes the hematocrit value approximately equal to $C_{Hb}/35$.

14. An apparatus for noninvasively monitoring hemoglobin concentration and oxygen saturation, comprising:
   a light radiation unit for sequentially radiating incident light beams having at least two wavelengths selected from a region in which an extinction coefficient for water is smaller than an extinction coefficient for hemoglobin, onto a predetermined site of the body that includes a blood vessel;
   a photodetector unit for receiving, at another site of the body, light beams transmitted through the predetermined site, converting the received light beams into an electrical signal, and outputting the converted electrical signal;
   a variation calculation unit for calculating light attenuation variation for each of the selected at least two wavelengths from the electrical signal and outputting the calculated light attenuation variation;
   a ratio calculation unit for calculating at least one ratio among the light attenuation variations sequentially input from the variation calculation unit and outputting the calculated at least one ratio of the light attenuation variations;
   a concentration calculation unit for calculating hemoglobin concentration in blood from the at least one ratio and outputting the calculated hemoglobin concentration; and
   a compression unit for compressing the predetermined site with a variable pressure,
   wherein the predetermined site is compressed by the compression unit to vary a thickness of the blood vessel with no pulses no greater than a predetermined value, and
   wherein the at least two wavelengths are externally selected to include at least two isobestic wavelengths.

15. The apparatus as claimed in claim 14, further comprising an oxygen saturation calculation unit for calculating oxygen saturation using the hemoglobin concentration input from the concentration calculation unit.

16. The apparatus as claimed in claim 15, further comprising a display unit for displaying the hemoglobin concentration and the oxygen saturation.

17. The apparatus as claimed in claim 14, further comprising a display unit for displaying the hemoglobin concentration.

18. The apparatus as claimed in claim 14, wherein the light radiation unit comprises a light emitting diode (LED) that sequentially radiates the incident light beams onto the predetermined site.

19. The apparatus as claimed in claim 14, wherein the light radiation unit comprises a laser diode (Ld) that sequentially radiates the incident light beams onto the predetermined site.

20. The apparatus as claimed in claim 14, wherein the light radiation unit comprises a lamp that sequentially radiates the incident light beams onto the predetermined site.

21. The apparatus as claimed in claim 14, wherein the light radiation unit comprises a photodiode that is made of a material selected from the group consisting of silicon (Si), germanium (Ge), and indium gallium arsenide (InGaAs) and sequentially radiates the incident light beams onto the predetermined site.

22. The apparatus as claimed in claim 14, further comprising at least one correction member having light transmitting and scattering characteristics similar to a soft issue of the body and disposed on an optical path of the incident light beams and on the outside of the predetermined site, wherein the thickness of the at least one correction member on the optical path is variable.

23. The apparatus as claimed in claim 22, wherein the at least one correction member is formed of one of the group consisting of: a liquid implemented in a form of gel, polystyrene beads, an intra-lipid, and a milk solution.

24. The apparatus as claimed in claim 14, wherein the light radiation unit sequentially radiates the incident light beams onto the predetermined site while compressing the predetermined site with a pressure by a predetermined variable weight of the light radiation unit.

25. The apparatus as claimed in claim 14, wherein the light radiation unit sequentially radiates the incident light beams onto the predetermined site while the pressure is applied by the compression unit.

26. The apparatus as claimed in claim 14, further comprising:

an amplifier for amplifying the electrical signal output from the photodetector units and outputting the amplified electrical signal;

a low-pass filter for filtering the low-frequency components of the amplified electrical signal and outputting the filtered low-frequency component; and an analog-to-digital converter for convening the filtered low-frequency component in analog form into digital form and outputting the converted digital low-frequency component to the variation calculation unit, wherein the variation calculation unit calculates the light attenuation variation for the respective selected wavelengths from the digital low-frequency component.

27. The apparatus of claim 14, wherein the concentration calculation unit comprises:

an address generator for generating an address based upon the relation between invasively measured hemoglobin concentrations input externally and the at least one ratio input from the ratio calculation unit and outputting the generated address; and a look-up table for predicting and outputting one of the invasively measured hemoglobin concentrations previously stored therein as the hemoglobin concentration in response to the address input from the address generator.

\* \* \* \* \*